United States Patent [19]

Nickell

[11] 4,033,755

[45] July 5, 1977

[54] RIPENING OF SUGARCANE BY USE OF AMMONIUM ISOBUTYRATE

[75] Inventor: Louis G. Nickell, Ellicott City, Md.

[73] Assignee: W. R. Grace & Co., New York, N.Y.

[22] Filed: Mar. 30, 1976

[21] Appl. No.: 671,790

[52] U.S. Cl. .................................... 71/113; 47/58; 127/42

[51] Int. Cl.² ........................................ A01N 9/24

[58] Field of Search .............. 71/106, 113; 127/42; 47/58

[56] References Cited

UNITED STATES PATENTS

| 2,951,754 | 9/1960 | Bishop | 71/113 X |
|---|---|---|---|
| 2,974,444 | 3/1961 | Lyon | 71/113 X |
| 3,001,862 | 9/1961 | Sowa | 71/113 X |
| 3,163,516 | 12/1964 | Weil | 71/113 X |
| 3,201,458 | 8/1965 | Scheverer | 71/106 X |
| 3,245,775 | 4/1966 | Koloman | 71/113 |
| 3,870,503 | 3/1975 | Nickell | 71/113 X |
| 3,897,241 | 7/1975 | Washio | 71/113 |
| 3,909,238 | 9/1975 | Nickell | 71/106 |

*Primary Examiner*—Sidney Marantz
*Attorney, Agent, or Firm*—Philip M. Pippenger; W. W. McDowell, Jr.

[57] ABSTRACT

Sucrose yield of sugarcane is increased by treating sugarcane a few weeks prior to harvest with ammonium isobutyrate as a sugarcane ripening agent.

5 Claims, No Drawings

RIPENING OF SUGARCANE BY USE OF AMMONIUM ISOBUTYRATE

BACKGROUND OF THE INVENTION

Considerable progress has been made in the last several years in increasing the sugar yield of sugarcane by improving the varieties being planted, enriching the soil with fertilizers and irrigating the soil in climates which do not naturally provide sufficient moisture for optimum plant growth. More recent efforts in improving sugar production have increasingly turned toward the use of chemicals in modifying the controlling of the physiological processes of sugarcane, particularly in ripening prior to harvest. See U.S. Pat. Nos. 3,245,775; 3,291,592; 3,482,959; 3,482,961; 3,493,361; 3,505,056; 3,660,072; 3,671,219; 3,482,961; 3,870,503; and 3,897,240, for example.

With some compounds previously suggested for this purpose, there has been some concern about their resistance to breakdown in the plant and their persistence in the soil when the intended use of the sugar is nutritive as opposed to industrial (e.g., in fermentation processes). Consequently, extensive efforts continue to be made in searching for effective chemical agents that can be used to modify the ripening of sugarcane so as to increase the sucrose yield therefrom.

Generally speaking, chemicals selected for evaluation have been of types which have been previously found active in work with other plants as plant hormones, herbicides or inhibitors of growth of terminal buds, or active in killing the spindle of cane upon topical micro-application, etc. However, among the compounds heretofore found to be useful for such other special purposes, surprisingly few have been found effective in controlling the ripening of sugarcane in the desirable manner. No predictable relationship has been recognized to date between (a) the chemical structure of such compounds, (b) their phytotoxic effects, or (c) their physiological effects on the morphogenetic development of the plant, and their activity in having positive effects on ripening. In other words, the effectiveness of a compound in controlling the ripening of sugarcane and thereby increasing sugar yield remains essentially unpredictable, and the search for suitable agents continues to be fundamentally empirical.

Isobutyrate salts of Group 1 of the Periodic Table and isobutyrate ethyl esters are known as sugarcane ripening agents. See L. G. Nickell, U.S. Pat. No. 3,870,503. However, ammonium isobutyrate (AIB) for this use is believed novel and upredictable.

OBJECTS OF THE INVENTION

It is an object of this invention to provide a new agent for controlling the ripening of sugarcane. A more specific object is to increase the sucrose yield of sugarcane by chemically treating it during its final ripening stages prior to harvest without introducing substantial toxicological hazards, and preferably without causing any visible damage to the cane plant such as drying of the spindle or other leaf.

Still more specifically, it is an object to increase the sucrose yield of sugarcane by treating it prior to harvest with a chemical agent which is sufficiently stable to provide the desired effect over a period of several weeks and thus give adequate operational flexibility, but which has a relatively low degree of persistence and is susceptible to autodecomposition or decomposition by soil bacteria. Compounds which increase the sucrose content of sugarcane only temporarily over a period of two or three weeks after application and then result in a substantial decrease are generally not desirable for the intended purpose.

SUMMARY OF THE INVENTION

It has now been discovered that excellent results in increasing the sucrose yield of sugarcane can be obtained by applying AIB as a sugarcane ripening agent to the cane at a time at least about 2 weeks and up to about 10 weeks before harvest.

DESCRIPTION OF SPECIFIC EMBODIMENTS

AIB is a crystalline, water-soluble solid under normal ambient conditions. This sugarcane ripening agent is generally applied to the sugarcane in an aqueous medium.

Good results are obtained when the sugarcane crop is treated at a rate in the range of from about 1 to about 40 pounds of AIB per acre of sugarcane, though higher rates of up to about 80 pounds or more per acre as well as rates lower than 1 pound per acre can be used. The optimum amount will vary somewhat depending on the specific treating composition applied.

In accordance with this invention, the sugarcane crop is treated with the sugarcane ripening agent at any time from 2 to 10 weeks before harvest, the preferred time for treatment being between about 3 and 8 weeks prior to harvest.

The sugarcane ripening agent is conveniently applied to the field in the form of an aqueous solution or suspension, e.g., a liquid composition which may be sprayed from a boom-spray or a solid dust composition where the active compound is diluted with an inert solid such as clay and which can be applied as a dust from an airplane.

With the type of boom-spray apparatus used in this work, it is convenient to apply the active ingredient to the sugarcane field in the form of a aqueous solution, suspension or emulsion having a concentration of active agent such that the application at a rate of from 5 to 20 gallons of liquid composition per acre will provide the required dosage of active chemical. However, the use of lower or higher gallonages may be preferred when a different dispensing mechanism is used.

Water is the preferred liquid carrier for AIB in practicing the present invention. Instead of using water as the carrier, nonphytotoxic mineral oils either as such or in the form of water-in-oil or oil-in-water emulsions may be used similarly in accordance with practices which are common in the art of treating vegetation with beneficial growth control agents. Other active ingredients are not required and are preferably omitted with the AIB being present as essentially the sole active ingredient in the solution of suspension.

The invention is additionally illustrated in connection with the following Examples which are to be considered as illustrative of the present invention. It should be understood, however, that the invention is not limited to the specific details of the Examples.

EXAMPLE 1

Part A — Preparation of Treating Compositions

A treating composition is prepared by weighing out 1.66 gram of a 60% aqueous solution of AIB. This solution is then diluted with water to exactly 8 ml to which one drop of commercial "Tergitol NPX" (liquid) surfactant is added with a medicine dropper. The resulting solution is agitated by shaking prior to application.

Part B — Application of AIB Composition to Cane

A 0.3 ml dose of aqueous solution containing 38 mg of AIB as described (equivalent to 4 lbs/acre) in Part A above was applied on the spindle area of each of 20 stalks of sugarcane in a commercial field in Hawaii, using a syringe with a fine needle as the applicator. Another group of 20 stalks in the same test were treated at the rate of 0.6 ml/stalk which is 76 mg/stalk and is equivalent to 8 lbs/acre. The age of the cane at the time of application was 20.25 months.

A set of 10 of these treated stalks from each group was harvested at 4 weeks after such treatment and another set of 10 was harvested at 5 weeks. In each harvest a set of 10 untreated stalks were also harvested as a control.

The top 15 joints of the treated can as well as those of similar untreated cane (control) are removed, combined and analyzed in terms of juice purity and pol percent cane, following the so-called "press method" developed by T. Tanimoto, Hawaiian Planters Record, 57, 133 (1964). "Pol percent cane" is a polarimetric determination and equals the percentage of sucrose if the latter is the only substance in the solution which will rotate the plane of polarized light. In any event, determination of the pol percent cane is a standard and effective method for determining the sucrose content of sugarcane.

The results are given in Table 1 below:

Table 1

| Compound | Time from Treatment to Harvest | | | |
|---|---|---|---|---|
| | 4 Weeks | | 5 Weeks | |
| | Juice Purity | Pol % Cane | Juice Purity | Pol % Cane |
| AIB (4 lb/acre) | 83.21 | 11.89 | 84.57 | 11.34 |
| AIB (8 lb/acre) | 84.06 | 11.97 | 85.87 | 12.25 |
| Control (Untreated) | 81.79 | 10.48 | 75.35 | 9.59 |

As is apparent, the application of AIB results in a very substantial improvement in both juice purity and pol percent cane.

EXAMPLE II

The procedure of Example I is repeated on stalks 21.5 months of age in a different field but with harvesting at 5 weeks and 6 weeks. The following results are obtained.

Table 2

| Compound | Time from Treatment to Harvest | | | |
|---|---|---|---|---|
| | 5 Weeks | | 6 Weeks | |
| | Juice Purity | Pol % Cane | Juice Purity | Pol % Cane |
| AIB (4 lb/acre) | 65.59 | 6.75 | 78.47 | 10.30 |
| AIB (8 lb/acre) | 77.49 | 10.09 | 77.83 | 10.35 |
| Control (Untreated) | 73.65 | 9.15 | 73.60 | 8.80 |

Generally, improvement in sucrose yield and juice purity results. The relatively poor results for 4 lb./5 weeks are considered somewhat anomalous in view of the excellent comparable data in Table 1.

The nature, scope, utility and effectiveness of the present invention have been described and specifically exemplified in the foregoing specification. However, it should be understood that these examples are not intended to be limiting and that the true scope of the invention to be protected is particularly pointed out in the appended claims.

What is claimed is:

1. A process for increasing the sugar yield of grown sugarcane which comprises applying an effective amount of ammonium isobutyrate as a sugarcane ripening agent to the cane at a time at least about 2 and up to about 10 weeks prior to harvest.

2. A process according to claim 1 wherein said sugarcane ripening agent is applied to the cane at a rate corresponding to from about 1 to about 80 pounds per acre.

3. A process according to claim 1 wherein the compound is applied to the cane at a time of between about 3 and about 8 weeks before harvest.

4. A process according to claim 2 wherein said sugarcane ripening agent is applied to the cane at a rate corresponding to from about 1 to about 40 pounds per acre.

5. A process according to claim 1 wherein the sugarcane ripening agent is applied to the cane at a rate of from 1 to about 40 pounds per acre and at a time of between about 3 and about 8 weeks before harvest.

* * * * *